United States Patent
Zander et al.

(10) Patent No.: US 12,251,143 B2
(45) Date of Patent: Mar. 18, 2025

(54) FUNNEL HOLE FOR INTRAMEDULLARY NAIL

(71) Applicant: Stryker European Operations Limited, Carrigtwohill (IE)

(72) Inventors: Nils Zander, Eckernförde (DE); Ilan Howling, Kiel (DE); Manfred Wieland, Kiel (DE)

(73) Assignee: Stryker European Operations Limited, Carrigtwohill (IE)

( * ) Notice: Subject to any disclaimer, the term of this patent is extended or adjusted under 35 U.S.C. 154(b) by 0 days.

(21) Appl. No.: 18/389,365

(22) Filed: Nov. 14, 2023

(65) Prior Publication Data

US 2024/0081879 A1    Mar. 14, 2024

Related U.S. Application Data

(63) Continuation of application No. 17/333,502, filed on May 28, 2021, now Pat. No. 11,819,253.

(60) Provisional application No. 63/031,701, filed on May 29, 2020.

(51) Int. Cl.
    *A61B 17/86*      (2006.01)
    *A61B 17/72*      (2006.01)

(52) U.S. Cl.
    CPC ........ *A61B 17/7208* (2013.01); *A61B 17/725* (2013.01); *A61B 17/864* (2013.01)

(58) Field of Classification Search
None
See application file for complete search history.

(56) References Cited

U.S. PATENT DOCUMENTS

| | | | |
|---|---|---|---|
| 4,928,679 | A | 5/1990 | Chagneau et al. |
| 5,035,697 | A | 7/1991 | Frigg |
| 5,041,115 | A | 8/1991 | Frigg et al. |
| 5,743,908 | A | 4/1998 | Kim |
| 5,779,704 | A | 7/1998 | Kim |
| 6,010,505 | A | 1/2000 | Asche et al. |
| 6,053,918 | A | 4/2000 | Spievack |
| 6,270,499 | B1 | 8/2001 | Leu et al. |
| 6,454,810 | B1 | 9/2002 | Lob |
| 6,547,791 | B1 | 4/2003 | Buhren et al. |

(Continued)

FOREIGN PATENT DOCUMENTS

| | | |
|---|---|---|
| DE | 102013005413 A1 | 10/2014 |
| DE | 102013005414 A1 | 10/2014 |

(Continued)

OTHER PUBLICATIONS

International Search Report for PCT/IB2021/000361 mailed Sep. 22, 2021 (5 pages).

*Primary Examiner* — Tessa M Matthews
(74) *Attorney, Agent, or Firm* — Lerner David LLP (57) ABSTRACT

An intramedullary nail may include a shank with a centerline defined along a length thereof. The intramedullary nail may also include a channel with a channel axis transverse to the centerline. The channel may have an obround shape in a first cross-sectional plane perpendicular to the channel axis at the centerline and a tapered profile in a second cross-sectional plane containing the channel axis. A proximal edge of the channel within the second cross-sectional plane may form a first angle relative to the channel axis and a distal edge of the channel within the second cross-sectional plane may form a second angle relative to the channel axis that is different from the first angle.

17 Claims, 9 Drawing Sheets

(56) References Cited

U.S. PATENT DOCUMENTS

| | | |
|---|---|---|
| 6,786,908 B2 | 9/2004 | Hover et al. |
| 6,808,527 B2 | 10/2004 | Lower et al. |
| 6,833,007 B2 | 12/2004 | Lob et al. |
| 7,232,442 B2 | 6/2007 | Sohngen et al. |
| 7,232,443 B2 | 6/2007 | Zander et al. |
| 7,410,488 B2 | 8/2008 | Janna et al. |
| 7,608,075 B2 | 10/2009 | Tornier |
| 7,655,009 B2 | 2/2010 | Grusin |
| 7,695,472 B2 | 4/2010 | Young |
| 7,771,428 B2 | 8/2010 | Siravo et al. |
| 7,867,231 B2 | 1/2011 | Cole |
| 7,914,532 B2 | 3/2011 | Shaver et al. |
| 7,947,043 B2 | 5/2011 | Mutchler |
| 8,066,706 B2 | 11/2011 | Schlienger et al. |
| 8,262,658 B2 | 9/2012 | Schlienger et al. |
| 8,287,540 B2 | 10/2012 | LeCronier et al. |
| 8,317,789 B2 | 11/2012 | LeCronier et al. |
| 8,425,574 B2 | 4/2013 | Huebner et al. |
| 8,460,294 B2 | 6/2013 | Overes |
| 8,568,413 B2 | 10/2013 | Mazur et al. |
| 8,568,414 B2 | 10/2013 | Siravo et al. |
| 8,668,695 B2 | 3/2014 | Schwammberger et al. |
| 8,679,120 B2 | 3/2014 | Frigg et al. |
| 8,709,055 B2 | 4/2014 | Beyar et al. |
| 8,771,271 B2 | 7/2014 | Overes |
| 8,771,272 B2 | 7/2014 | LeCronier et al. |
| 8,790,343 B2 | 7/2014 | McClellan et al. |
| 8,906,024 B2 | 12/2014 | Schlienger et al. |
| 9,044,283 B2 | 6/2015 | Simon |
| 9,050,149 B2 | 6/2015 | LeCronier et al. |
| 9,072,552 B2 | 7/2015 | Simon et al. |
| 9,101,417 B2 | 8/2015 | Beyar et al. |
| 9,192,416 B2 | 11/2015 | Siravo et al. |
| 9,308,031 B2 | 4/2016 | Elghazaly et al. |
| 9,358,049 B2 | 6/2016 | Simon et al. |
| 9,414,871 B2 | 8/2016 | Huebner et al. |
| 9,433,448 B2 | 9/2016 | Ehmke et al. |
| 9,474,557 B2 | 10/2016 | Schwammberger et al. |
| 9,532,817 B2 | 1/2017 | Overes |
| 9,545,273 B2 | 1/2017 | Howling et al. |
| 9,572,606 B2 | 2/2017 | Frank et al. |
| 9,668,791 B2 | 6/2017 | Khong et al. |
| 9,770,273 B2 | 9/2017 | Guitelman |
| 9,782,206 B2 | 10/2017 | Mueckter et al. |
| 9,795,412 B2 | 10/2017 | Sinha |
| 9,861,418 B2 | 1/2018 | Matityahu et al. |
| 9,943,346 B2 | 4/2018 | Elghazaly et al. |
| 9,993,277 B2 | 6/2018 | Krinke et al. |
| 10,028,777 B2 | 7/2018 | Beyar et al. |
| 10,034,696 B2 | 7/2018 | Mueckter et al. |
| 10,039,582 B2 | 8/2018 | Nardini |
| 10,251,691 B2 | 4/2019 | Hedgeland et al. |
| 10,258,380 B2 | 4/2019 | Sinha |
| 10,299,847 B2 | 5/2019 | Rossney et al. |
| 10,307,197 B2 | 6/2019 | Hedgeland et al. |
| 10,314,626 B2 | 6/2019 | Koay et al. |
| 10,398,482 B2 | 9/2019 | Lutz et al. |
| 10,456,180 B2 | 10/2019 | Huebner et al. |
| 10,463,416 B2 | 11/2019 | Rossney et al. |
| 2002/0111629 A1 | 8/2002 | Phillips |
| 2004/0010252 A1 | 1/2004 | Zander et al. |
| 2006/0200141 A1 | 9/2006 | Janna et al. |
| 2007/0123874 A1 | 5/2007 | Czartoski et al. |
| 2007/0123876 A1 | 5/2007 | Czartoski et al. |
| 2010/0114097 A1 | 5/2010 | Siravo et al. |
| 2011/0022049 A1 | 1/2011 | Huebner et al. |
| 2012/0330313 A1 | 12/2012 | Grady et al. |
| 2013/0053847 A1 | 2/2013 | Siravo et al. |
| 2013/0289563 A1 | 10/2013 | Overes |
| 2014/0031823 A1 | 1/2014 | Mazur et al. |
| 2014/0066932 A1 | 3/2014 | Appenzeller et al. |
| 2014/0277181 A1 | 9/2014 | Garlock |
| 2014/0296853 A1 | 10/2014 | Wolter |
| 2014/0296854 A1 | 10/2014 | Wolter |
| 2015/0216574 A1 | 8/2015 | Huebner et al. |
| 2016/0051295 A1 | 2/2016 | Nakamura et al. |
| 2016/0310176 A1 | 10/2016 | Van Dyke et al. |
| 2018/0078291 A1 | 3/2018 | Rossney et al. |
| 2018/0125546 A1 | 5/2018 | Matityahu et al. |
| 2018/0146992 A1 | 5/2018 | Prien et al. |
| 2018/0250041 A1 | 9/2018 | Rossney et al. |
| 2018/0310971 A1 | 11/2018 | Nardini |
| 2019/0038326 A1 | 2/2019 | Hedgeland et al. |
| 2019/0175240 A1 | 6/2019 | Hedgeland et al. |
| 2019/0192189 A1 | 6/2019 | Sinha |
| 2019/0247103 A1 | 8/2019 | Hedgeland et al. |
| 2019/0314065 A1 | 10/2019 | Petersik et al. |
| 2019/0314106 A1 | 10/2019 | Matityahu et al. |
| 2019/0343569 A1 | 11/2019 | Hedgeland et al. |
| 2020/0015875 A1 | 1/2020 | Rossney et al. |
| 2020/0054375 A1 | 2/2020 | Huebner et al. |
| 2020/0069318 A1 | 3/2020 | Machamer et al. |

FOREIGN PATENT DOCUMENTS

| | | |
|---|---|---|
| DE | 102010048052 B4 | 6/2015 |
| EP | 1342453 A2 | 9/2003 |
| EP | 1356777 A2 | 10/2003 |
| EP | 1570797 A1 | 9/2005 |
| EP | 1346696 B1 | 10/2005 |
| EP | 1759649 A1 | 3/2007 |
| EP | 1779794 A1 | 5/2007 |
| EP | 1779795 A1 | 5/2007 |
| EP | 1199995 B1 | 9/2007 |
| EP | 1839610 A1 | 10/2007 |
| EP | 1443865 B1 | 11/2009 |
| EP | 2926750 A1 | 10/2015 |
| EP | 3466357 A1 | 4/2019 |
| JP | 2015217263 A | 12/2015 |
| JP | 2015217264 A | 12/2015 |
| WO | 2005/092219 A1 | 10/2005 |
| WO | 2012103354 A1 | 8/2012 |

FUNNEL HOLE FOR INTRAMEDULLARY NAIL

CROSS REFERENCE TO RELATED APPLICATION

The present application is a continuation of U.S. patent application Ser. No. 17/333,502, filed on May 28, 2021, which claims the benefit of the filing date of U.S. Provisional Patent Application No. 63/031,701 filed May 29, 2020, the disclosures of which are hereby incorporated herein by reference.

BACKGROUND

Intramedullary nails are known solutions for treating injuries to bone, such as fractures or breaks. For example, it is known to use an intramedullary nail to treat a fracture in a body of a femur, or to use an intramedullary nail in cooperation with a lag screw to treat a fracture in a femoral neck. Such intramedullary nails may have elongate shapes, including a relatively thin and cannulated shank extending from a head of the nail that is intended to fit through a medullary cavity of the bone being treated. The cannulation along the entire length of the nail is used for a surgeon to insert k-wires for guiding the nail during insertion into the intramedullary canal of the long bone such as a femur or tibia.

In some applications, one or more locking screws are inserted through the bone and through corresponding channels located near a distal end of the shank. Because the shank may deflect while being driven into the bone by an amount that is difficult to predict with certainty, workable locations and angles for accurate placement of the locking screws is likely to vary between patients. Additional steps may be required before inserting the locking screws, such as scanning or imaging the bone and nail after the nail is implanted to determine the final location of the channels.

BRIEF SUMMARY

An intramedullary nail may be designed such that locking screws may be inserted through channels at a distal end of the nail after the nail is inserted into a long bone while taking into account any flexure of the nail that occurs during insertion. The flexion of the nail occurs due to the fact that the intramedullary canal of a long bone is curved and therefore the inserted nail follows the anatomy of the bone. Such a nail may be designed such that a drill may be inserted through the bone at a given location and angle relative to the bone, or relative to a head of the nail, without contacting a proximal or distal edge of the corresponding channels.

To that end, part of the channels may have a funnel shape. The channels may generally be of constant cross-section, such as being cylindrical in shape, and extend in a direction perpendicular to the centerline of the nail, except for the funnel shaped portions. The funnel shape may taper from being wider at one side of the nail to narrower at the other side. The taper may be along only a part of a depth of the channel, and the channel may include an inflection point separating a tapered portion from a portion of constant size. The channels may be of a constant width relative to a lateral direction of a shank of the nail, but may taper from longer to shorter relative to a lengthwise direction of the shank of the nail. Such channels may therefore have an obround shape at least at a wider end thereof, and through at least part of a depth thereof.

In another aspect, an intramedullary nail may include a shank with a centerline defined along a length thereof. The intramedullary nail may also include a channel with a channel axis transverse to the centerline. The channel may have an obround shape in a first cross-sectional plane perpendicular to the channel axis at the centerline and a tapered profile in a second cross-sectional plane containing the channel axis. A proximal edge of the channel within the second cross-sectional plane may form a first angle relative to the channel axis and a distal edge of the channel within the second cross-sectional plane may form a second angle relative to the channel axis that is different from the first angle.

In some arrangements, opposed proximal and distal ends of the channel may each be defined by a round end extending along respective non-parallel axes. Opposed sides of the channel may be planar and extend between the two round ends to define the obround shape.

In some arrangements, the channel is fully internally threaded.

In some arrangements, the channel defines a circular opening at a surface of the shank.

In some arrangements, the two non-parallel axes may each intersect the centerline.

In some arrangements, the first angle may be non-zero and the second angle may be zero.

In some arrangements, the nail may include an obround opening in the shank that feeds into the channel, and at least part of a perimeter of the obround opening may be chamfered.

In some arrangements, an angle between the two non-parallel axes may be between 3° and 7°.

In some arrangements, the angle between the two non-parallel axes may be 6.5°.

In another aspect, the shank may be capable of elastic deformation across a range of deflection of a distal tip of the shank on the second cross-sectional plane. A ratio of the range of deflection of the distal tip of the shank to a total length of the nail may be at least 1:30. A rectangular area may exist on the second cross-sectional plane that may extend through the channel without crossing a proximal or distal edge of the channel at any position within the range of tip travel.

In some arrangements, the ratio of the range of deflection of the distal tip of the shank to the total length of the nail may be 1:24.

In some arrangements, the shank may define a bore extending along the centerline and dividing the channel into two aligned apertures.

In another aspect, a method for treating injury to a femur may include inserting an intramedullary nail into the femur generally along the anatomical axis of the femur. The nail may include a shank with a centerline defined along a length thereof. The shank may have a channel with a channel axis transverse to the centerline. The channel may have an obround shape in a first cross-sectional plane perpendicular to the channel axis at the centerline and a tapered profile on a second cross-sectional plane containing the channel axis at the centerline. The method may also include inserting a screw through a predetermined location of the femur.

In some arrangements, the nail may include an obround opening in the shank that feeds into the channel. The nail may be implanted in the femur with the obround opening oriented in an anterior direction relative to the femur.

In some arrangements, the nail may be implanted in the femur such that the tapered profile narrows toward a posterior direction relative to the femur.

In some arrangements, the method may further include drilling through the femur and the channel at a predetermined location of the femur from the anterior direction toward the posterior direction.

In some arrangements, the screw may engage at least a portion of the channel to accommodate flexion of the intramedullary nail that occurs during implantation.

In some arrangements, a method of designing an intramedullary nail may include estimating an anticipated range of flexion of a shank of an intramedullary nail on a flexion plane corresponding to flexion of the nail during a procedure for implanting the nail in a bone. The method may include defining a fixed position for a cylindrical fixation element relative to a head of the nail located at a proximal end of the nail. The fixed position may be such that the cylindrical fixation element would extend transverse to and intersect the shank at any position of the shank within the anticipated range of flexion. The method may also include selecting respective locations and angles for a proximal extremity of a channel disposed through a distal half of the shank and a distal extremity of the channel such that the cylindrical fixation element located at the fixed position would extend through the channel without crossing the proximal extremity or the distal extremity of the channel at any degree of flexion of the shank within the anticipated range of flexion.

In some arrangements, the method may include defining an additional fixed position for an additional cylindrical fixation element. The method may include selecting respective locations and angles for proximal and distal extremities of an additional channel disposed through the distal half of the shank such that the additional cylindrical fixation element located at the additional fixed position would extend through the additional channel without crossing the proximal or distal extremity of the additional channel at any degree of flexion of the shank within the anticipated range of flexion.

In some arrangements, a method for treating injury to a femur using the intramedullary nail may include inserting the nail into the femur generally along the anatomical axis of the femur while allowing flexion of the nail within the femur. The method may also include, after the nail is inserted into the femur, inserting a screw through the femur and channel at a location and angle relative to the head of the nail corresponding to the fixed position of the cylindrical fixation element.

DETAILED DESCRIPTION

Figure 1A:
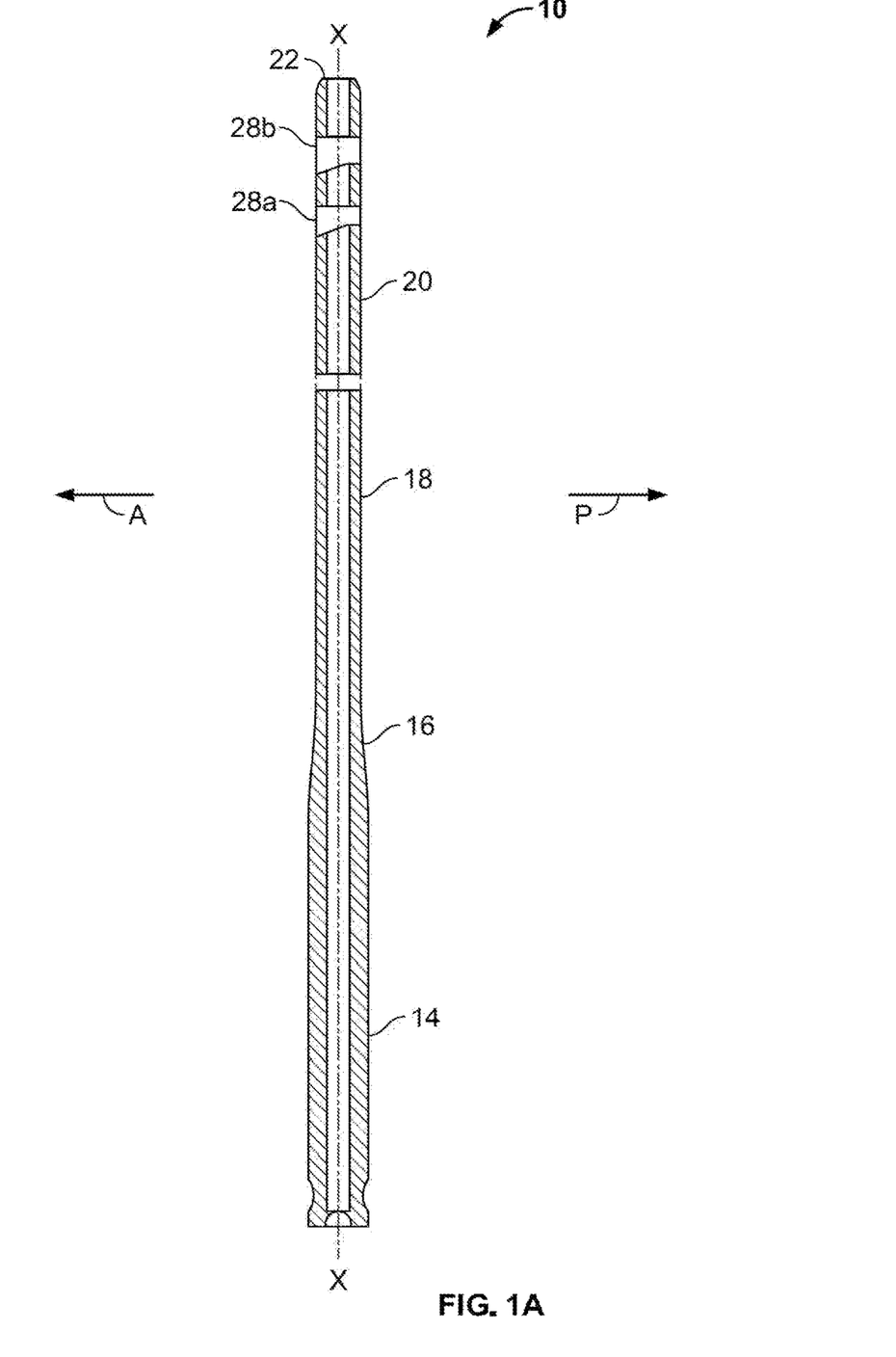
FIG. 1A is a cross-sectional elevation view of a nail according to a first arrangement.
Figure 1B:
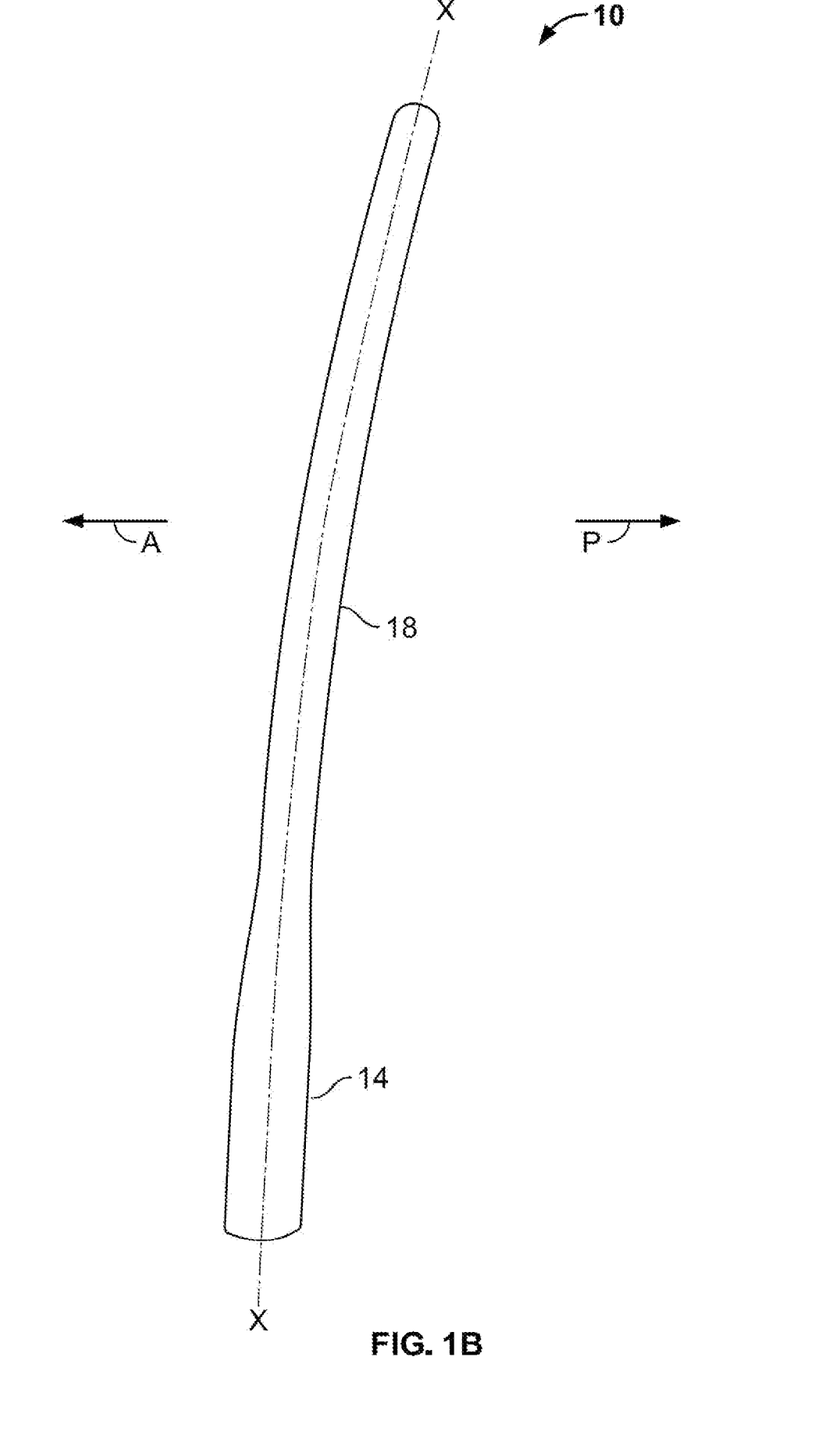
FIG. 1B is an elevation view of a nail according to a second arrangement.

An intramedullary nail 10 illustrated in FIG. 1A includes a head 14, a cone 16 tapering to a narrower diameter from the head 14, and a shank 18 extending from the cone 16. The nail 10 extends along a centerline X. The centerline X is illustrated as straight in FIG. 1A, but the shank 18 is flexible with respect to the head 14, meaning the centerline X may have a curved profile depending on the shank's 18 state of flexure. The shank 18 may have a non-linear resting position, which may, for example, include the centerline X curving toward a posterior direction P with increasing distance from the head 14 such as in the alternative arrangement shown in FIG. 1B. The shank 18 may therefore be able to curve further toward the posterior direction P than an opposite anterior direction A.

A distal portion 20 of the shank terminates in a point 22. The distal portion 20 illustrated herein is a distalmost half of the shank 18. The distal portion 20 includes at least one channel 28 extending therethrough. In the illustrated arrangement, the distal portion 20 includes a first channel 28a and a second channel 28b extending anterior to posterior through the nail 10. The second channel 28b is closer to the point 22 and has a greater width along the centerline X than the first channel 28a.

Figure 2A:
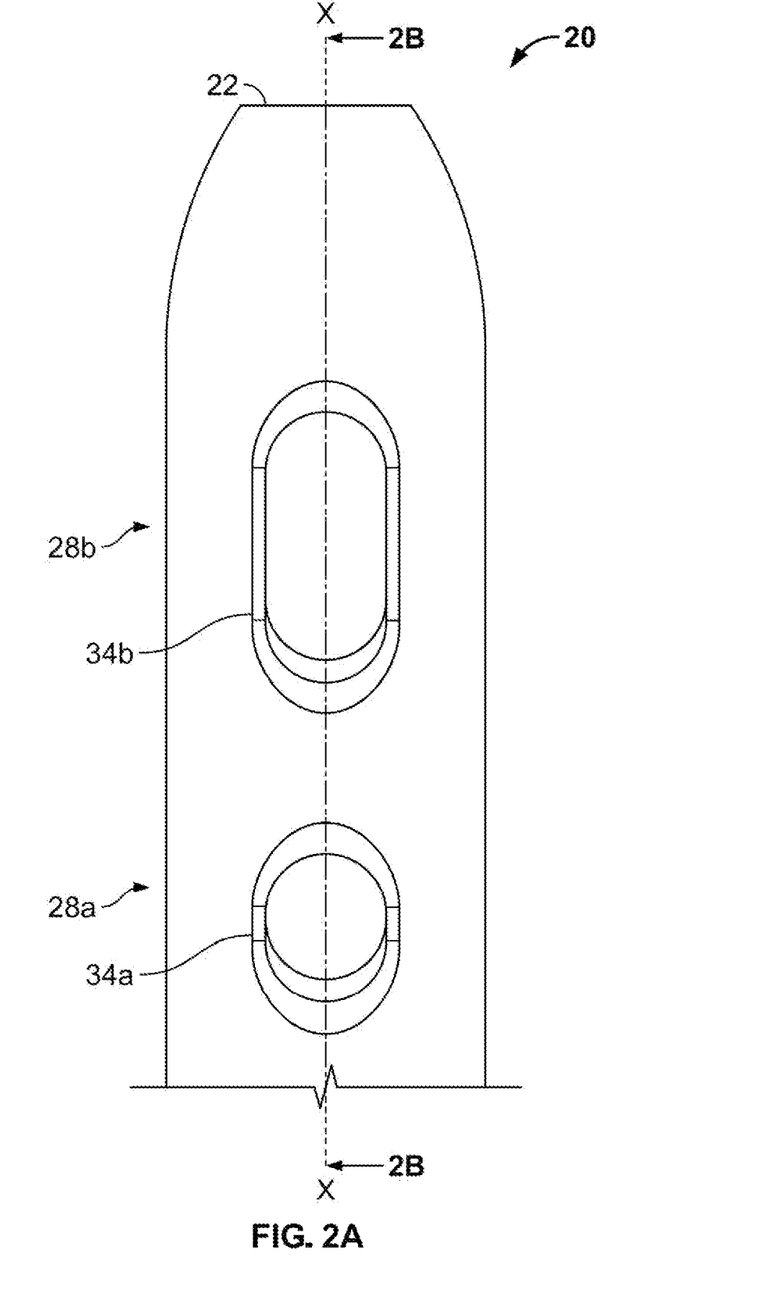
FIG. 2A is a side elevation view of a tip portion of the nail of FIG. 1A.

As shown in more detail in FIG. 2A, the first and second channels 28a, 28b have first and second chamfered anterior openings 34a, 34b, respectively. Both anterior openings 34a, 34b have obround shapes from the perspective of FIG. 2A extending lengthwise parallel to the centerline X. Here, "obround" refers to any of a stadium shape, an orthographic projection of a capsule, a shape including two opposed semicircular, or approximately semicircular, edges joined by two parallel lines, or shapes generally similar to the foregoing. However, "obround shape" is used in an approximate sense to accounts for the fact that the curved perimeter of the shank 18 gives the anterior openings 34a, 34b non-planar profiles.

Figure 2B:
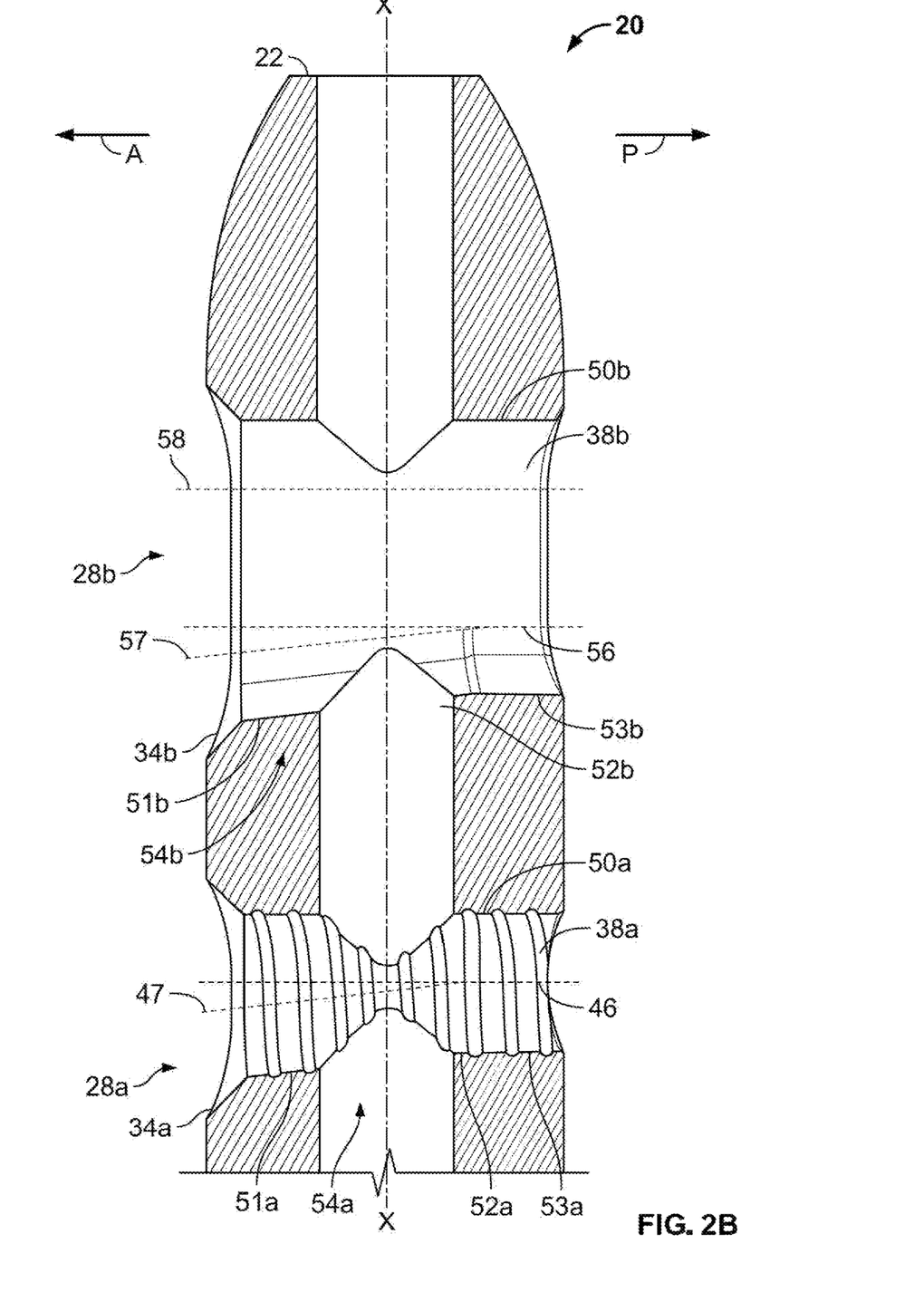
FIG. 2B is a cross-sectional view along line 2B-2B of FIG. 2A.
Figure 2C:
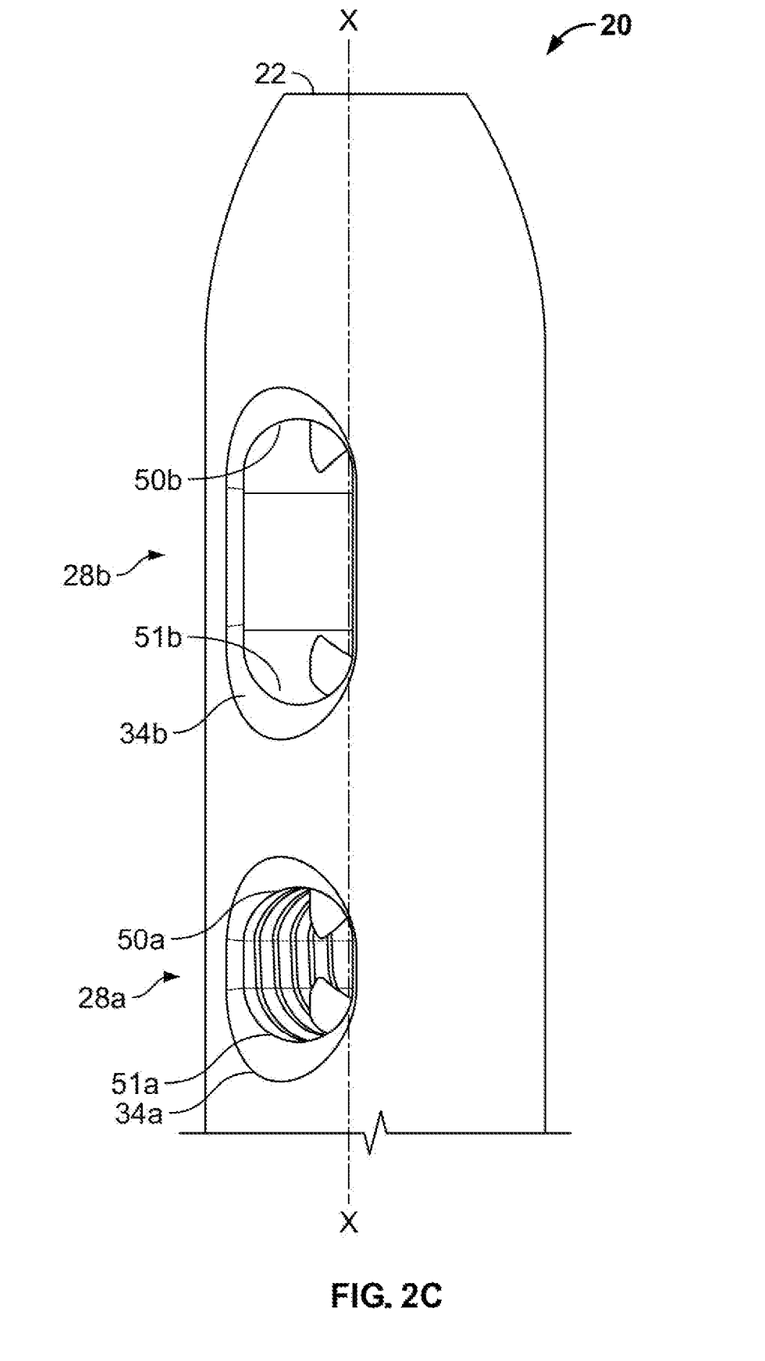
FIG. 2C is another side elevation view of the tip portion of the snail shown in FIG. 2A

Turning to FIGS. 2B and 2C, the first and second channels 28a, 28b further include first and second posterior openings 38a, 38b, respectively. The first posterior opening 38a is circular, having a diameter equal to a lateral width of the first anterior opening 28a, while the second posterior opening 38b is obround, having an equal lateral width to that of the second anterior opening 28b, but a lesser width parallel to the centerline X.

The first channel 28a defines a centered orthogonal axis 46 extending perpendicular to the centerline X and through a centerpoint of the first posterior opening 38b. A first distal edge 50a of the first channel 28a extends parallel to the centered orthogonal axis 46. A distal part of the first channel 28a defines a cylinder centered on the centered orthogonal axis 46. The funnel shape of the first channel 28a is further defined by a first skew axis 47 angled with respect to the centered orthogonal axis 46. Here, "angled" is used to mean that the first skew axis 47 extends at a non-zero angle relative to the centered orthogonal axis 46. The first skew axis 47 extends parallel to a first ramped portion 51a of a proximal edge 54a of the first channel 28a. In a preferred arrangements, the first skew axis 47 extends at an angle of 6.5° relative to the centered orthogonal axis 46. In other arrangements, this angle can be in the range of 3.5° to 9.5°, or 4° to 8°, or 6° to 7°. The first ramped portion 51a extends distally and posteriorly away from the first anterior opening 34a to a first inflection point 52a at which the first channel 28a reaches a circular cross sectional shape. The volume below this first inflection point 52a to first posterior opening 38a is a cylindrical zone of first channel 28a, as indicated above. The volume above first inflection point 52a to first anterior opening 34a at the distal side of first channel 28a between centered orthogonal axis 46 and first distal edge 50a is also part of a cylindrical volume, i.e. a half cylinder, of first channel 28a. The volume above first inflection point 52a to first anterior opening 34a at the proximal side of first channel 28a between centered orthogonal axis 46 and first ramped portion 51a is a conical zone of first channel 28a. Together, these 3 volumes make up the entire volume of first channel 28a.

The first ramped portion 51a also extends along a most proximal extremity of a half cylinder defined by the first channel 28a that extends along the first skew axis 47 between the first inflection point 52a and the first anterior opening 34a. The first proximal edge 54a is defined by the first ramped portion 51a, the first inflection point 52a, and a first orthogonal portion 53a, collectively. The first orthogonal portion 53a of the first proximal edge 54a extends parallel to the centered orthogonal axis 46 between the first inflection point 52a and the first posterior opening 38a. As such, an anterior portion of the first channel 28a defined between the first anterior opening 34a and the first inflection point 52a has a funnel shape. Specifically, the anterior portion of the first channel 28a tapers to be narrower along a length of the shank 18 from the first proximal opening 34a to the first inflection point 52a, thereby defining a funnel shape. A posterior portion of the first channel 28a defined between the first inflection point 52a and the first posterior opening 38a has a cylindrical shape.

The first channel 28a is threaded around its interior as illustrated. Despite the variation in the perimeter of the first channel 28a, the first channel 28a is threaded at a constant pitch from the first posterior opening 34a to the first posterior opening 38a. An object with exterior threading, such as a screw, may therefore threadingly engage the first channel 28a along an entire length of the first channel 28a. For more details regarding exemplary screws suitable for engagement with any of the nails of the present disclosure, reference may be made to International Publication Number 2019/111041, corresponding to International Patent Application Number PCT/IB2017/057688, filed on Dec. 6, 2017. Because the angle between first skew axis 47 and centered orthogonal axis 46 is relatively small, the threads of a screw securely engage the threaded portion at any part of first channel 28a despite whether the screw may not be exactly parallel to centered orthogonal axis 46 about which the threads of first channel 28a are defined.

The second channel 28b similarly defines a second distal edge 50b that extends perpendicular to the centerline X and a second proximal edge 54b that includes a second ramped portion 51b defining a funnel shape in cooperation with the second distal edge 50b, a second orthogonal portion 53b extending parallel to the second distal edge 50b, and a second inflection point 52b between the second ramped portion 51b and the second orthogonal portion 53b. The second channel 28b defines a proximal orthogonal axis 56 and a distal orthogonal axis 58, both perpendicular to the centerline X at their respective locations. A distal portion of the second channel 28b defines a half of a cylinder centered on the distal orthogonal axis, and a proximal portion of the second channel 28b between the second inflection point 52b and the second posterior opening 38b defines a half of a cylinder centered on the proximal orthogonal axis 56. The second channel 28 therefore has an obround cross section between the second inflection point 52b and the second posterior opening 38b. The second channel 28b of the illustrated arrangement is not threaded, and may non-threadingly receive a transverse element such as a locking screw or nail for restraining movement of the nail 10 within the bone.

The second ramped portion 51b extends both distally and posteriorly from the second anterior opening 34b to the second inflection point 52b. A second skew axis 57 is defined parallel to the ramped portion 51b. In various arrangements, the second skew axis 57 extends at an angle of between 3° and 7°, or 6.5°, relative to the proximal orthogonal axis 56. A proximal portion of the channel 28b between the second anterior opening 34b and the second inflection point 52b defines a half of a cylinder centered on the second skew axis 57. An anterior portion of the second channel between the second anterior opening 34b and the second inflection point 52b therefore has a funnel shape that narrows relative to the centerline X as it extends further in the posterior direction P, but has a constant width relative to a lateral direction that is perpendicular to the proximal orthogonal axis 56, distal orthogonal axis 58, and second skew axis 57.

The foregoing description pertains to the illustrated arrangement, and nails 10 according to other arrangements differ in some respects to suit different applications. For example, in some alternative arrangements, the orthogonal axes 46, 57, and 58, the distal edges 50a, 50b, and the orthogonal portions 53a, 53b of the proximal edges 54a, 54b extend at non-perpendicular angles relative to the centerline X at their respective locations along the centerline X.

Figure 3:
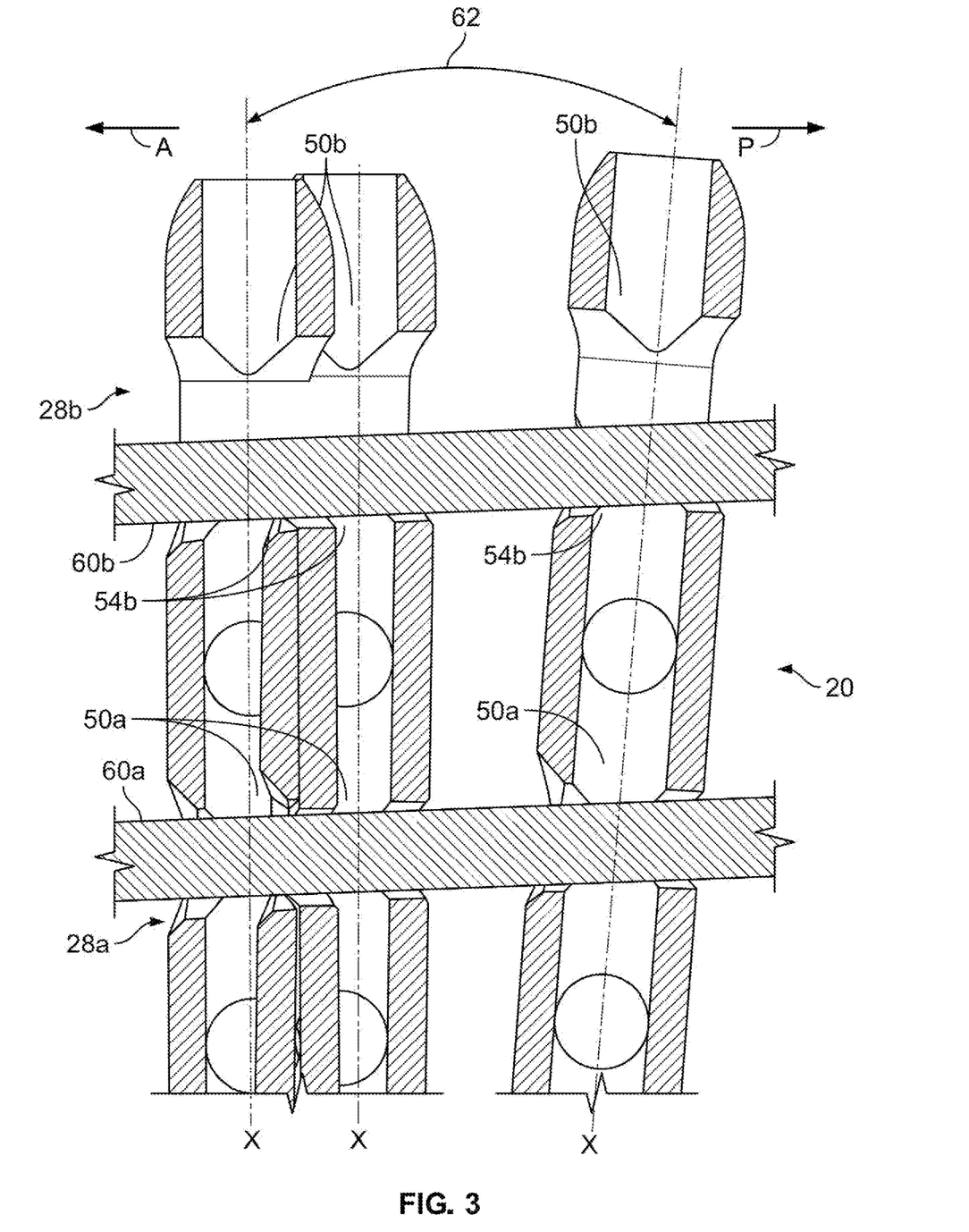
FIG. 3 is a cross-sectional elevation view of the nail of FIG. 1A in three degrees of deflection.

The nail 10 is flexible such that typical forces on the shank 18 during insertion of the nail 10 into bone may cause the nail 10 to deflect in the anterior direction A or posterior direction P within an expected range of deflection 62 as illustrated in FIG. 3. In various arrangements, the expected degree of deflection can be determined empirically or by theoretical analysis of the nail 10, such as finite element analysis. A first theoretical cylinder 28a extends through the first channel 28a and a second theoretical cylinder 28b extends through the second channel 28b throughout the expected range of deflection 62. The funnel shapes of the anterior portions of the first channel 28a and second channel 28b enable the distal portion 20 of the shank 18 to travel across the entire expected range of deflection 62 while the first theoretical cylinder 60a and second theoretical cylinder 60b remain stationary relative to the head 14 without either of the cylinders 60a, 60b crossing the boundary of either of the proximal edges 154a, 154b or distal edges 150a, 150b of the channels 28a, 28b. As such, it is possible to install the nail 10 in a bone, then insert a cylindrical drill bit having a similar diameter to the theoretical cylinders 60a, 60b in both channels 28a, 28b, followed by cylindrical locking elements such as bone screws of slightly larger diameter than the theoretical cylinders 60a, 60b at predetermined locations relative to the head 14 without measuring actual deflection of the nail 10 in situ. Because the funnel shapes of the channels 28a, 28b accommodate the theoretical cylinders 60a, 60b throughout the expected range of deflection 62, the drill or drills will not damage the channels 28a, 28b, or any threading therein, and cylindrical locking elements inserted through the bone at the same position relative to the head 14 as the cylinders 60a, 60b can be expected to extend cleanly through the channels 28a, 28b and to engage a portion of the threaded channel to facilitate locking. Further, because of the elongated threading of the first channel 28a, a blindly inserted bone screw can be expected to threadingly engage the first channel 28a regardless of the actual degree of deflection. Though the first channel 28a is illustrated as fully threaded, in some alternative arrangements the first channel 28a is only partially threaded. For example, in some arrangements, only the distal or proximal half of the first channel 28a is threaded.

In some arrangements, the nail 10 may be constructed such that the expected range of deflection 62 extends further in the posterior direction than in the anterior direction relative to the head 14, as shown in FIG. 3. Flexibility of the nail 10 may vary as appropriate for a given procedure. For example, the flexibility of the nail 10 may depend on the size, shape, and density of the bone for which the nail 10 is intended and the anticipated force to be applied to the nail 10 during the procedure. In some arrangements, a ratio of the range of deflection 62 to a total length of the nail 10 is at least 1:30. In further arrangements, the ratio of the range of deflection to the total length of the nail is 1:24. From left to right, FIG. 3 shows the distal portion 20 in an extreme anterior position, a middle position, and an extreme posterior position. The middle position is closer to the extreme anterior position than the extreme posterior position. In some arrangements, the middle position is three times farther from the extreme posterior position than the extreme anterior position. The inclination toward posterior deflection can be designed into the nail 10 by, for example, designing the nail to have a neutral position, meaning a position the nail 10 assumes in the absence of external forces, wherein the centerline X curves toward the posterior direction away from the head 14.

Figure 4:
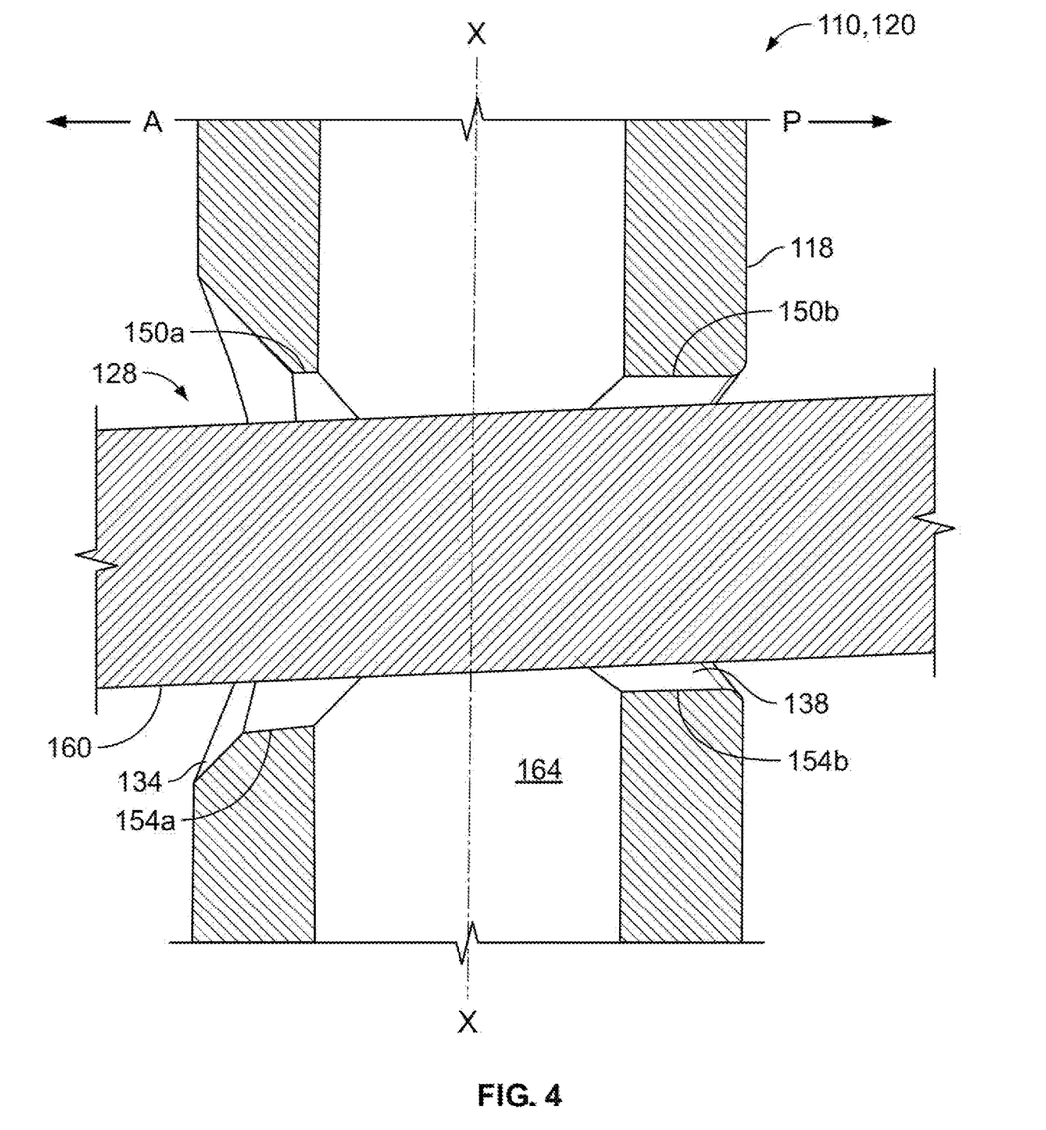
FIG. 4 is a cross-sectional elevation view of a portion of a nail according to a third arrangement.

A portion of a nail 110 according to an alternative arrangement is illustrated in FIG. 4. The shank 118 is cannulated and contains a bore 164 extending along the centerline X. A channel 128 extending through the shank 118 is therefore provided by a chamfered anterior opening 134 and a posterior opening 138 on opposite sides of the bore 164. The anterior opening 134 is defined between an anterior distal edge 150a and an anterior proximal edge 154a, and the posterior opening 138 is defined between a posterior distal edge 150b and a posterior proximal edge 154b. The posterior opening 138 has a circular cross-sectional shape, and a cross-sectional shape of the anterior opening 134 has a thickness defined perpendicular to the centerline X that is equal to a diameter of the posterior opening 138. The anterior opening 134 has an obround cross-sectional shape such that a distance between the anterior proximal edge 150a and the anterior distal edge 154a is greater than the diameter of the posterior opening 138. Similar to the nail 10 as illustrated in FIG. 3, the nail 110 is designed such that a theoretical cylinder 160 at a given position relative to a head (not pictured) of the nail 110 may extend through the channel 128 at any degree of deflection of the shank 118 within a range of deflection expected to result from insertion of the nail 110 into a bone. Specifically, respective locations and angles of the edges 150a, 150b, 154a, 154b of the channel 128 permit the shank 110 to deflect throughout the expected range of deflection while the theoretical cylinder 160 remains stationary without any of the edges 150a, 150b, 154a, 154b contacting the theoretical cylinder.

In other arrangements, the distal portion 20 includes differing numbers and arrangements of anterior to posterior channels. For example, the distal portion 20 may include only one, or three or more, anterior to posterior channels, and the relative widths along the centerline X of the anterior to posterior channels may have any pattern along the centerline X. For example, the channel with the greatest width along the centerline X may be a middle or proximal most channel of the channels included in the distal portion.

Nails 10, 110 according to any of the foregoing examples may be designed according to empirically derived or mathematically determined values. Specifically, one or more sets of general dimensions of a nail 10, 110, such as length and diameter, may be predetermined. Ranges of curvature of the nail 10, 110 to be expected during an implanting procedure may be estimated by experimentation with simulated implanting procedures, mathematically, such as by finite element analysis, or by a combination of experimental and mathematical processes, for each predetermined set of general dimensions. Angles and dimensions of channels through the nails 10, 110 of the various predetermined general dimensions may then be determined in view of the expected range of curvature and the diameters of any associated drills or bone screws. Specifically, each channel for a given set of predetermined general dimensions may be located, angled, and dimensioned such that an associated drill may be driven through the bone and channel at a predetermined location and angle relative to a head of the nail 10, 110 without damaging the channel or any threading internal to the channel, and a bone screw may be engaged through the channel at a predetermined location and angle relative to a head of the nail 10, 110, after the nail 10, 110 has been implanted, for any position of the nail 10, 110 within the expected range of curvature. A nail 10, 110 designed according to the foregoing process may therefore be implanted into a bone and secured in place with transverse bone screws without an intervening step of determining the actual degree of curvature of the nail 10, 110.

Figure 5:
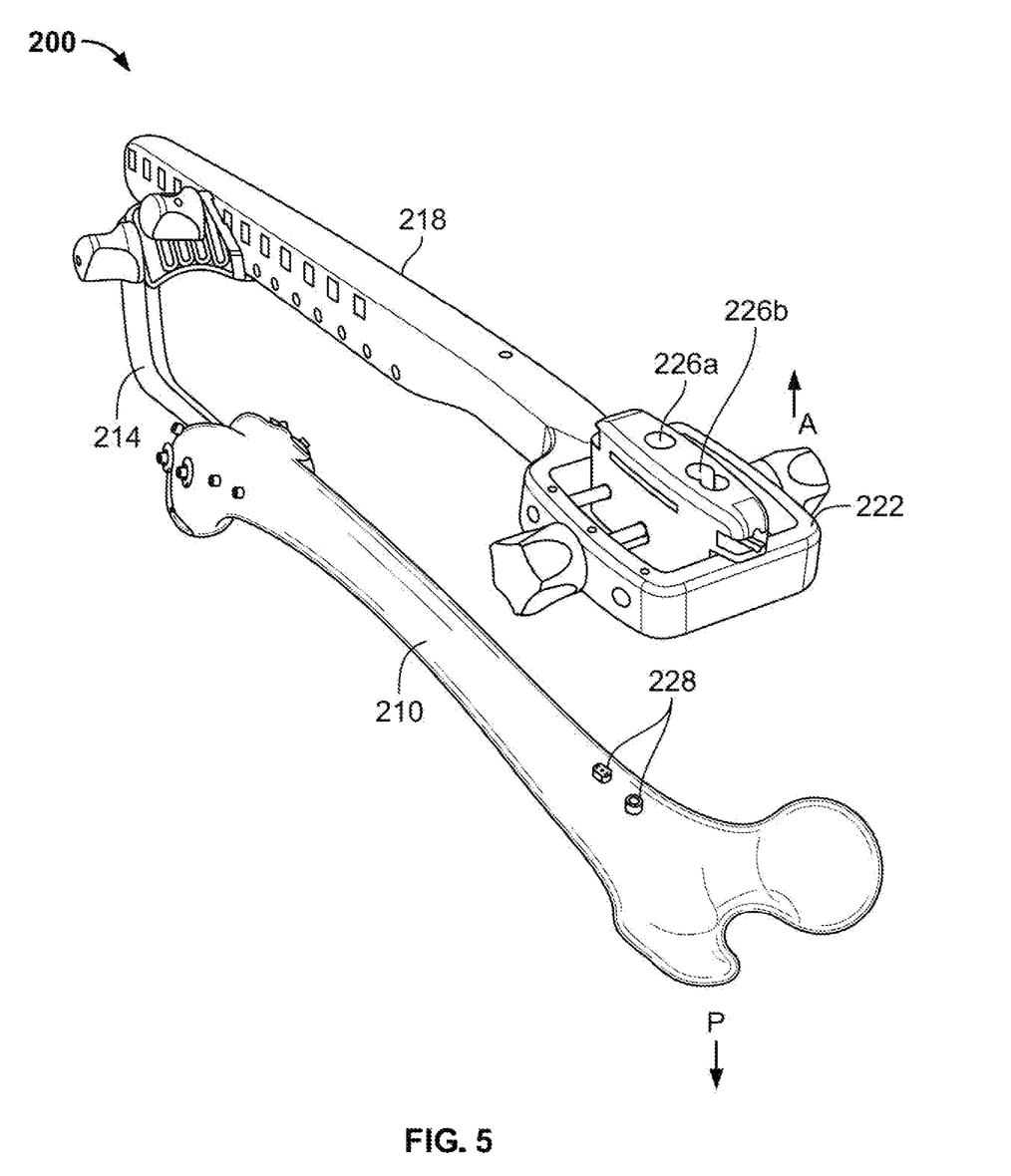
FIG. 5 is a perspective view of a targeting device for use with the nails of FIG. 1A, 1B, or 4.

Illustrated in FIG. 5 is a targeting device 200 for preparing a femur 210 in a retrograde guided targeting drilling procedure. This procedure secures a nail 10, 110 after the nail 10, 110 has been inserted into the femoral canal. The targeting device 200 includes a bracket 214 connectable to the head of the nail 10, 110. The bracket 214 holds an arm 218 of the targeting device 200 at a location that can be adjusted for each specific use depending on the patient anatomy. The arm 218 ends in a block 222 containing two guide holes 226a, 226b for guiding a drill and a fastener through the femur 210 and nail 10. Guide holes 226a, 226b are specifically dimensioned and positioned to coincide with channels 28a, 28b of nail 10 to allow locking of nail 10 within the femur. That is, block 222 is positioned with respect to the femur 210 such that both guide holes 226a, 226b will direct the drill and subsequent screws or pins through the channels 28a, 28b, respectively, without the drill contacting the edges of the channel.

Figure 6:
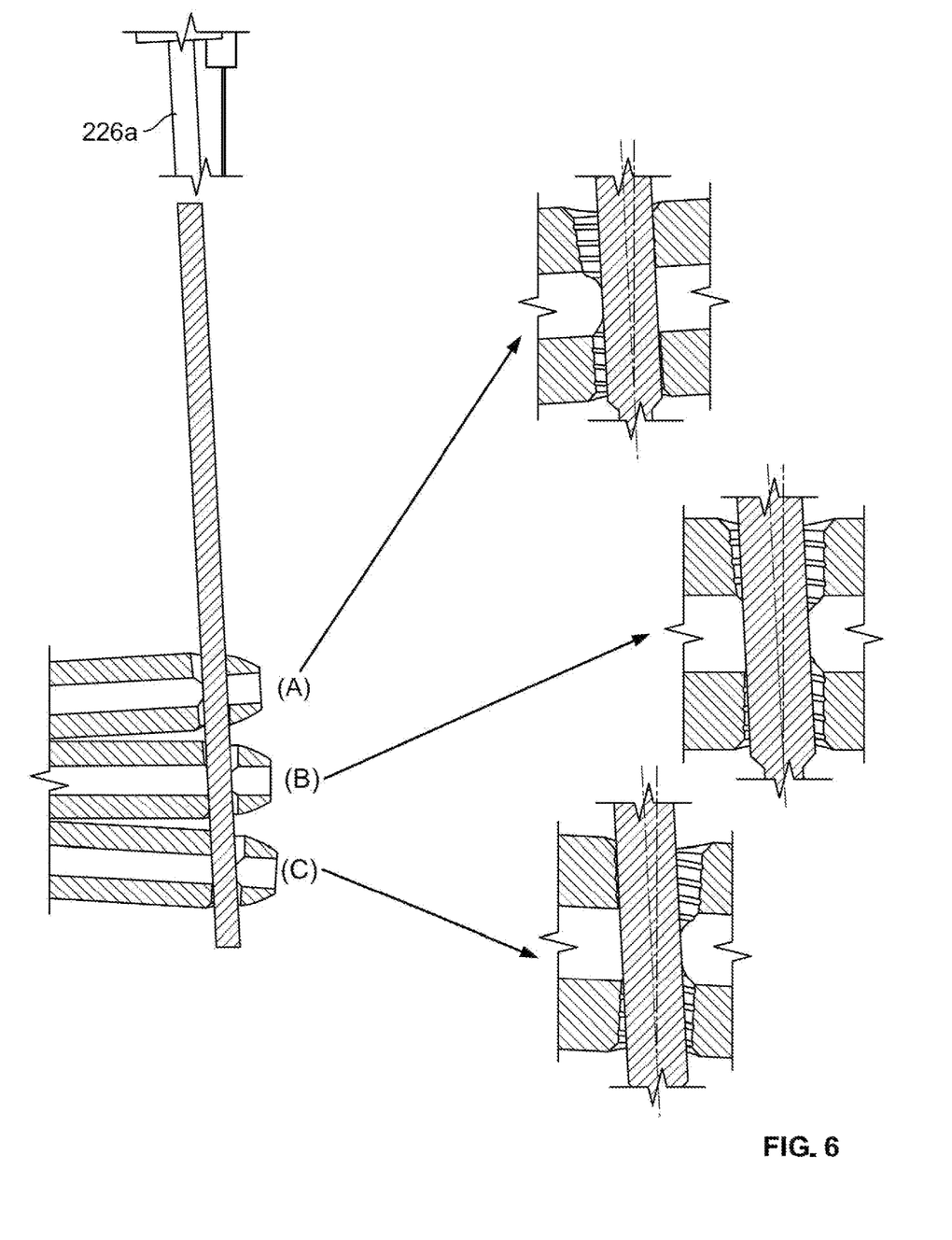
FIG. 6 is a cross-sectional elevation view of the targeting device of FIG. 5 guiding a drill into the nail of FIG. 1A, 1B, or 4 through various stages of deflection.

Guide hole 226a is cylindrical and is angled at 3° from an axis that is perpendicular to a centerline of block 222, which is designed to be parallel to the centerline X of nail 10 when nail 10 is at rest or undeflected in the position (B) shown in FIG. 6. The 3° angle corresponds to the geometry of channel 28a and allows predrilling with a drill, of 4.2 mm for example, without any metal contact in deflected and undeflected nails when used with channel 28a. Also shown in FIG. 6 are a position (A) depicting the nail in anterior deflection, and a position (C) depicting the nail in posterior deflection. The 3° angle of guide hole 226a coincides with the geometry and orientation of channel 28a so that a drill bit or a screw passed through guide hole 226a would pass through a central portion of channel 28a with nail 10 at rest, i.e. along an axis coincident with or between first skew axis 47 and centered orthogonal axis 46 depending on the flexion state of nail 10. Guide hole 226a is tilted at 3° such that an axis through the center of guide hole 226a and centered orthogonal axis 46 of first channel 28a intersect at the center of the uppermost part of the cylindrical zone of channel 28a, i.e. aligned with first inflection point 52a. Guide hole 226b is similarly angled at 3° with respect to proximal orthogonal axis 56 of second channel 28b to provide the same cooperation between guide hole 226b and second channel 28b as is described above between guide hole 226a and first channel 28a. Guide hole 226b is oblong for static/dynamic locking in second channel 28b.

Since guide hole 226a is tilted at 3°, first channel 28a is configured so that a drill passed through first channel 28a will not contact either first ramped portion 51a or first distal edge 50a despite any deflection in nail 10. This is shown in FIG. 6, where position (A) coincides with anterior deflection of nail 10, yet nail 10 is aligned such that first distal edge 50a is close to axial alignment with the drill bit. In position (C) showing posterior deflection of nail 10, nail 10 is aligned such that first ramped portion 51a is close to axial alignment with drill bit. The angle of 6.5° of first ramped portion 51a and the angle of 0° of first distal edge 50a have been empirically determined so that the 3° angle of 226a can facilitate drilling without metal contact or any alteration of the interior threads of first channel 28a. The 0° angle of first distal edge 50 represents the locking hole position without the funnel function, such that it represents the orientation of all round holes perpendicular to the nail axis. The design was chosen so that the least material was removed compared to the round hole of previous designs. This testing has focused on the range of deflection angles of nail 10 given various contours and shapes of femurs to focus the angle range to a zone that encompasses substantially all potential values of deflection. This results in substantially all procedures resulting in no metal contact between the drill and first channel 28a. Accordingly, during targeting and drilling through the targeting device, the nail should not be damaged, either in undeflected or in deflected position.

After guide holes 226a, 226b are used to guide the drill through the femur 210, fasteners or screws 228 may be inserted through the drilled holes and channels 28a, 28b, 128 to secure the nail 10, 110 to the femur 210. Since channels 28a, 28b, 128 are obround, the screws 228 are able to engage with the internal threads of channels 28a, 28b, 128 despite whatever deflection may exist in nail 10. For example, channel 28a has a lateral width throughout that is the same as the diameter of channel 28a in the cylindrical zone below the first inflection point 52a. This is despite the fact that the proximal-distal dimension of channel 28a increases in a direction upward and away from first inflection point 52a. in that way, when a screw 228 is inserted at an extreme deflection state of nail 10, it will engage the screw threads at first ramped portion 51a or first distal edge 50a, in addition to engaging the internal threads at the lateral sides of channel 28a and the internal threads of the cylindrical zone below the first inflection point 52a. At any angle between these extremes, the screw 228 will engage the screw threads at least at the lateral sides of channel 28a and the internal threads of the cylindrical zone below the first inflection point 52a. Although the threaded connection may not be a perfect match, the range of angles permits threaded engagement of the screw within channel 28a despite the angle at which the screw 228 is inserted. Once the screw enters the cylindrical zone between first orthogonal portion 53a and first distal edge 50a, which is below first inflection point 52a, the cylindrical nature of this portion of channel 28a reorients the screw so that it is finally positioned perpendicular to the axis of the nail like in normal round holes. Of course in some instances this reorientation of the screw may not result in a completely perpendicular orientation. In those instances, the geometry and contouring of channel 28a is utilized to facilitate secure locking of a screw 228 regardless of what deflection may be present in an implanted nail 10, which eliminates the need for a user to be concerned with finely tuned and precise angling of screw insertion during a procedure. Of course, channel 28a is described herein as an example in this method, and channels 28b and 128 are designed in the same manner while accounting for their oblong shape.

Although the concepts herein have been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

The invention claimed is:

1. An intramedullary nail comprising:
a shank with a centerline defined along a length thereof;
said shank having a first channel with a first channel axis perpendicular to the centerline, the first channel having an obround shape in a first cross-sectional plane perpendicular to the first channel axis at the centerline and a tapered profile in a second cross-sectional plane containing the first channel axis, wherein the first channel is internally threaded; and
said shank having a second channel with a second channel axis perpendicular to the centerline, the second channel having an obround shape in a third cross-sectional plane perpendicular to the second channel axis at the centerline and a tapered profile in the second cross-sectional plane.

2. The intramedullary nail of claim 1, wherein opposed proximal and distal ends of the first channel are each defined by a round surface extending along respective non-parallel axes, and opposed sides of the first channel are planar and extend between the two round surfaces to define the obround shape.

3. The intramedullary nail of claim 2, wherein an extension portion of the first channel defines a circular opening at a surface of the shank.

4. The intramedullary nail of claim 2, wherein the two non-parallel axes each intersect the centerline.

5. The intramedullary nail of claim 2, wherein a portion of a proximal edge of the first channel within the second cross-sectional plane forms a first angle relative to the first channel axis and a distal edge of the first channel within the second cross-sectional plane forms a second angle relative to the first channel axis that is different from the first angle, and the first angle is non-zero, and the second angle is zero.

6. The intramedullary nail of claim 2, wherein the nail includes an obround opening in the shank that feeds into the first channel, and at least part of a perimeter of the obround opening is chamfered.

7. The intramedullary nail of claim 2, wherein an angle between the two non-parallel axes is between 3° and 7°.

8. The intramedullary nail of claim 7, wherein the angle between the two non-parallel axes is 6.5°.

9. The intramedullary nail of claim 2, wherein:
a portion of the round surface of the proximal end of the first channel defines a half of a cylinder centered on the proximal axis, and a portion of the round surface of the distal end of the first channel defines a half of a cylinder centered on the distal axis.

10. The intramedullary nail of claim 1, wherein:

the shank is capable of elastic deformation across a range of deflection on the second cross-sectional plane, a ratio of a distance travelled by a distal tip of the shank between opposite ends of the range of deflection to a total length of the nail being at least 1:30; and a rectangular area exists on the second cross-sectional plane that does not intersect a proximal or distal edge of the first channel at any position of the shank within the range of deflection.

11. The intramedullary nail of claim 10, wherein the ratio of the range of deflection of the distal tip of the shank to the total length of the nail is 1:24.

12. The intramedullary nail of claim 1, wherein the shank defines a bore extending along the centerline and dividing the first channel into two aligned passages and the second channel into two aligned passages.

13. A method for treating injury to a bone, comprising:

inserting an intramedullary nail into an intramedullary canal of the bone generally along the anatomical axis of the bone, wherein the nail includes:

a shank with a centerline defined along a length thereof;

said shank having a first channel with a first channel axis perpendicular to the centerline, the first channel having an obround shape in a first cross-sectional plane perpendicular to the first channel axis at the centerline and a tapered profile in a second cross-sectional plane containing the first channel axis at the centerline, wherein the first channel is internally threaded; and said shank having a second channel with a second channel axis perpendicular to the centerline, the second channel having an obround shape in a third cross-sectional plane perpendicular to the second channel axis at the centerline and a tapered profile in the second cross-sectional plane;

inserting a screw through a predetermined location of the bone such that the screw threadingly engages at least a portion of the first channel; and inserting a screw through a predetermined location of the bone such that the screw engages at least a portion of the second channel.

14. The method of claim 13, wherein the nail includes an obround opening in the shank that feeds into the first channel, and the nail is implanted in the bone with the obround opening oriented in an anterior direction relative to the bone.

15. The method of claim 14, wherein the nail is implanted in the bone such that the tapered profile of the first channel narrows toward a posterior direction relative to the bone.

16. The method of claim 15, further comprising drilling through the bone and the first channel at a predetermined location of the bone from the anterior direction toward the posterior direction.

17. The method of claim 13, wherein the screw engages at least a portion of the first channel to accommodate flexion of the intramedullary nail that occurs during implantation.

* * * * *